US00PP18299P3

(12) United States Plant Patent
Korlipara

(10) Patent No.: US PP18,299 P3
(45) Date of Patent: Dec. 11, 2007

(54) ***COREOPSIS* PLANT NAMED 'STRAWBERRY LEMONADE'**

(50) Latin Name: ***Coreopsis* hybrid**
Varietal Denomination: Strawberry Lemonade

(75) Inventor: Harini Korlipara, Canby, OR (US)

(73) Assignee: Terra Nova Nurseries, Canby, OR (US)

( * ) Notice: Subject to any disclaimer, the term of this patent is extended or adjusted under 35 U.S.C. 154(b) by 117 days.

(21) Appl. No.: 11/344,356

(22) Filed: Jan. 30, 2006

(65) Prior Publication Data

US 2007/0180592 P1 Aug. 2, 2007

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP15,979 P2 * 9/2005 Bell ..... Plt./263

* cited by examiner

*Primary Examiner*—Wendy C. Haas
(74) *Attorney, Agent, or Firm*—Klarquist Sparkman LLP

(57) ABSTRACT

A new and distinct *Coreopsis* plant named 'Strawberry Lemonade' characterized by yellow foliage, red purple flowers, and a dwarf habit.

1 Drawing Sheet

Botanical designation: *Coreopsis* hybrid (parents unknown).

Variety denomination: 'Strawberry Lemonade'.

Cross reference to: co-pending applications for *Coreopsis* 'Pink Lemonade' (U.S. application Ser. No. 11/343,831, filed Jan. 30, 2006) and 'Cherry Lemonade' (U.S. application Ser. No. 11/343,832, filed Jan. 30, 2006).

BACKGROUND OF THE INVENTION

The present invention relates to a new and distinct plant of *Coreopsis* and given the cultivar name 'Strawberry Lemonade'. *Coreopsis* is in the family Asteraceae. This new cultivar originated from offspring located at Terra Nova Nurseries in Canby, Oreg. and reproduced in tissue culture where further selections where made. This selection was made for its cherry red flowers.

SUMMARY OF THE INVENTION

The following traits have been repeatedly observed and are determined to be the unique characteristics of 'Strawberry Lemonade'. These characteristics in combination distinguish 'Strawberry Lemonade' as a new and distinct cultivar:

1. Golden yellow foliage.
2. Red purple daisy type flowers.
3. Dwarf mounding habit.
4. Very free flowering.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one year old *Coreopsis* 'Strawberry Lemonade' growing in the ground in the garden in August in Canby, Oreg.

DETAILED PLANT DESCRIPTION

The following is a detailed description of the new *Coreopsis* cultivar based on observations of a one-year-old specimen grown in the ground in full sun under typical outdoor conditions in the garden in August in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:

*Type.*—Herbaceous perennial.
*Hardiness.*—USDA Zones 9–10.
*Size.*—40 cm wide and 25 cm tall to top of flowers.
*Form.*—Low mound with freely branching stems.
*Vigor.*—Good.
*Roots.*—Fibrous, freely branching, fine and White 155A in color. Roots develop easily from cuttings.

Stem:

*Type.*—Ascending.
*Size.*—20 cm tall and 1 to 2 mm wide.
*Internode length.*—12 to 30 mm.
*Surface.*—Glabrous.
*Color.*—Yellow Green 146C.

Leaf:

*Type.*—Simple.

*Shape.*—Linear.

*Arrangement.*—Opposite.

*Length.*—25 to 40 mm, sessile.

*Width.*—1 to 2 mm.

*Margins.*—Entire.

*Apex.*—Acute.

*Base.*—Attenuate.

*Surface texture.*—Glabrous, soft and smooth to the touch.

*Venation.*—Pinnate.

*Color.*—Top side — Yellow, Yellow 10A with a green main vein Yellow Green 146C to Yellow Green 146A where shaded. Bottom — same as top side.

Inflorescence:

*Type.*—Long stalked terminal heads of daisy type flowers.

*Peduncle.*—7 cm tall and 1 mm wide, glabrous, Yellow 10A to Yellow Green 146C where shaded.

Flower:

*Type.*—Perfect, zygomorphic.

*Size.*—2.5 to 3.5 cm wide and 8 mm deep.

*Ray petals.*—Number — 8. Shape: Obovate with the tip three lobed with lobes obtuse and the central lobe the longest, base attenuate, margins entire. Size: Grows to 17 mm long, 8 mm wide. Surface texture: Glabrous, soft and velvety to the touch. Color: Ray flower, topside — Between Greyed Purple 187B and Red Purple 71A. Ray, bottom side — Closest to Purple 71A, but duller.

*Cone.*—Shape: Conic, deeper with maturity. Size: 7 mm wide and becoming 5 mm deep with maturity. Color: Brown 200B when in bud, opening to orange, Orange 24A with a dark background, Greyed Purple 187A.

*Disc flowers.*—5 mm long and 1 mm wide, tubular, 4 lobed, Greyed Purple 187A at the apex to Orange 24A in middle and Yellow orange 20B near base.

*Pistil.*—6 mm long, Orange 24A overall, extruding, 2-branched stigma, ovary 1.5 mm long, style 4 mm long.

*Stamen.*—4, filaments 3 mm long, extruding, Black 202A.

*Pollen color.*—Yellow 12C.

*Bloom period.*—June through September in Canby, Oreg.

*Fragrance.*—Light, daisy like.

Seed: None produced.

*Fertility.*—Infertile.

Disease and pests: *Coreopsis* are susceptible to mildew and fungal spots. None of these have been observed on plants grown under commercial conditions in Canby, Oreg.

COMPARISONS TO SIMILAR *COREOPSIS*

Compared to *Coreopsis* 'Limerock Ruby' (U.S. Plant patent application Ser. No. 20030066114), this new cultivar has the same flower size. It is different in its yellow foliage, dwarf habit and red purple flower color.

I claim:

1. A new and distinct *Coreopsis* plant named 'Strawberry Lemonade' as herein illustrated and described.

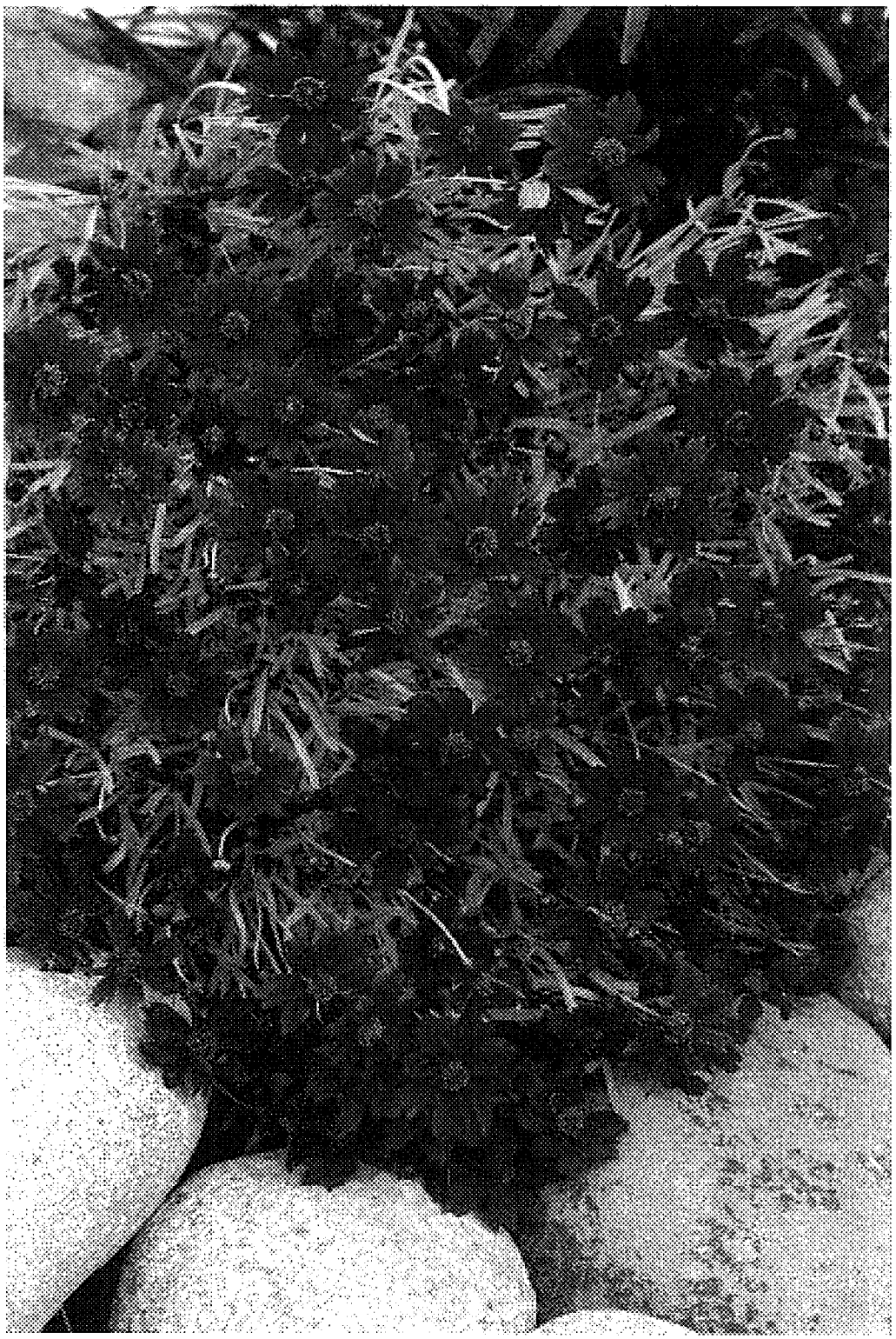

* * * * *